US 6,524,844 B2

(12) United States Patent
Brieden et al.

(10) Patent No.: US 6,524,844 B2
(45) Date of Patent: Feb. 25, 2003

(54) PROCESS FOR PREPARING OPTICALLY ACTIVE 1-AMINO-4-(HYDROXYMETHYL) CYCLOPENT-2-ENE DERIVATIVES

(75) Inventors: Walter Brieden, Brig-Gils (CH); Kay-Sara Etter, Niedergampel (CH); Michael Petersen, Visp (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/888,068

(22) Filed: Jun. 22, 2001

(65) Prior Publication Data
US 2002/0042108 A1 Apr. 11, 2002

Related U.S. Application Data

(63) Continuation of application No. PCT/EP99/10382, filed on Dec. 23, 1999.
(60) Provisional application No. 60/145,999, filed on Jul. 29, 1999.

(30) Foreign Application Priority Data

Dec. 23, 1998 (EP) .............................. 98124570

(51) Int. Cl.⁷ ................................. C12P 41/00
(52) U.S. Cl. ...................... 435/280; 435/68.1; 435/195; 435/227; 564/133; 564/443; 560/129
(58) Field of Search ................. 564/133, 443; 435/68.1, 195, 227, 280; 560/129

(56) References Cited

U.S. PATENT DOCUMENTS

| 6,137,007 A | 10/2000 | Bernegger et al. ............ 215/42 |
| 6,368,850 B1 | 4/2002 | Bernegger-Egli ............ 435/280 |
| 2002/0010360 A1 | 1/2002 | Brieden et al. ................ 233/6 |

FOREIGN PATENT DOCUMENTS

| EP | 878548 A2 | 11/1998 | ........... C12P/17/18 |
| EP | 926131 A2 | 6/1999 | ......... C07C/213/00 |
| WO | 92/18444 | 10/1992 | |
| WO | 9745529 | * 12/1997 | |

OTHER PUBLICATIONS

Campbell et al., *J. Org. Chem.*, 1995, 60, 4602–4616.
Mahmoudian et al., *Enzyme Microb. Technol.*, 1992, 14, 911–916.
Jaeger et al. *Trends in Biotechnology*, vol. 16, 1998, 396–403.

* cited by examiner

Primary Examiner—Shailendra Kumar
(74) Attorney, Agent, or Firm—Darby & Darby

(57) ABSTRACT

The invention discloses a new method for producing enantiomer-enriched 1-amino-4-(hydroxymethyl)-cyclopent-2-ene derivatives of the general formulae (I) and (II) in which $R^1$ is hydrogen or a possibly substituted $C_{1-8}$ alkyl radical, aryl radical or cycloalkyl radical and $R^2$ is acyl. According to said method a racemic 1-amino-4-(hydroxymethyl)-cyclopent-2-ene derivative of general formula (III), in which $R^1$ has the meaning given above, is converted using a hydrolase and in the presence of an acylation agent 7 Claims, No Drawings

PROCESS FOR PREPARING OPTICALLY ACTIVE 1-AMINO-4-(HYDROXYMETHYL) CYCLOPENT-2-ENE DERIVATIVES This is a continuation of international application ser. No. PCT/EP99/10382, filed Dec. 23, 1999, and claims the benefit of Provisional application Ser. No. 60/145,999, filed Jul. 29, 1999, the entire disclosure of which is hereby incorporated by reference.

FIELD OF THE INVENTION

The present invention relates to a novel process for preparing enantiomerically enriched 1-amino-4-(hydroxymethyl)cyclopent-2-ene derivatives of the general formulae:

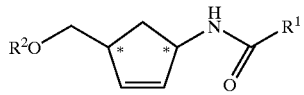

I

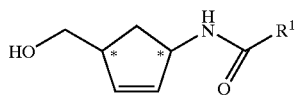

II in which $R^1$ is hydrogen, alkyl, aryl or cycloalkyl and $R^2$ is acyl, and in particular to reacting them further to give the corresponding enantiomerically enriched 1-amino-4-(hydroxymethyl)cyclopent-2-ene compounds of the formula IV

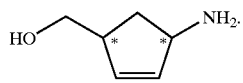

IV

BACKGROUND OF THE PRIOR ART

Enantiomerically enriched 1-amino-4-(hydroxymethyl)cyclopent-2-ene of the formula IV, such as, for example, (1R,4S)-1-amino-4-(hydroxymethyl)cyclo-pent-2-ene, is an important intermediate in the preparation of carbocyclic nucleosides, such as, for example, carbovir (Campbell et al., J. Org. Chem. 1995, 60, 4602–4616).

Hereinbelow, "enantiomerically enriched" compounds are understood as compounds having an enantiomeric excess (ee) of more than 20%.

A number of processes for preparing (1R,4S)-1-amino-4-(hydroxymethyl)cyclopent-2-ene have been known up until now. WO 97/45529, for example, describes a biotechnological process for preparing (1R,4S)-1-amino-4-(hydroxymethyl)cyclopent-2-ene starting from racemic cis-N-acetyl-1-amino-4-(hydroxymethyl)cyclopent-2-ene using microorganisms which employ the latter as the only carbon source, as the only nitrogen source or as the only carbon and nitrogen source. This process has the disadvantage that it has to be carried out in a fermenter.

OBJECT OF THE INVENTION

It is the object of the present invention to provide an alternative, simple and cost-efficient process for preparing enantiomerically enriched 1-amino-4-(hydroxymethyl) cyclopent-2-ene derivatives of the formula I and II and enantiomerically enriched 1-amino-4-(hydroxymethyl) cyclopent-2-ene compounds of the formula IV.

According to the invention, the object is achieved by converting a racemic 1-amino-4-(hydroxymethyl)cyclopent-2-ene derivative of the general formula

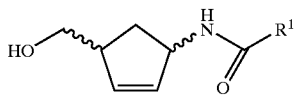

III in which $R^1$ is hydrogen, an optionally substituted, linear or branched $C_{1-8}$-alkyl radical, aryl radical or cycloalkyl radical using a hydrolase in the presence of an acylating agent into the enantiomerically enriched 1-amino-4-(hydroxymethyl)-cyclopent-2-ene derivatives of the general formulae

I

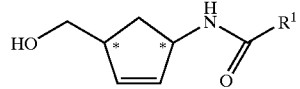

II in which $R^1$ is as defined above and $R^2$ is acyl.

DETAILED DESCRIPTION OF THE INVENTION

The present invention is directed to a process for preparing enantiomerically enriched 1-amino-4-(hydroxymethyl) cyclopent-2-ene derivatives of the general formulae

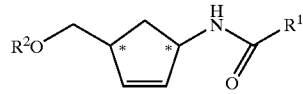

I

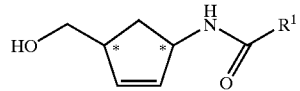

II wherein $R^1$ is hydrogen or an optionally substituted $C_{1-8}$-alkyl radical, aryl radical or cycloalkyl radical and $R^2$ is acyl, and wherein a racemic 1-amino-4-(hydroxymethyl) cyclopent-2-ene derivative of the general formula:

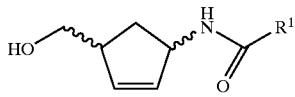

III in which $R^1$ is as defined above is reacted using a hydrolase in the presence of an acylating agent.

Another embodiment of the present invention is directed to a process for preparing enantiomerically enriched 1-amino-4-(hydroxymethyl)cyclopent-2-ene derivatives of the general formula comprising a) converting a racemic 1-amino-4-(hydroxymethyl) cyclopent-2-ene derivative of the general formula

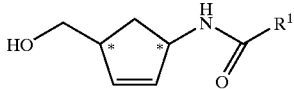
III in which $R^1$, as defined in claim 1; using a hydrolase in the presence of an acylating agent into enantiomerically enriched

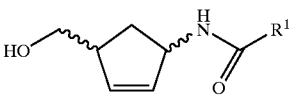
I wherein $R^1$ and $R^2$, as defined in claim 1; and b) chemically hydrolyzing the 1-amino-4-(hydroxymethyl)cyclopent-2-ene derivatives of the general formula I into the corresponding enantiomers of the general formula II.

A further embodiment of the present invention is directed to a process for preparing enantiomerically enriched 1-amino-4-(hydroxymethyl)cyclopent-2-ene of the formula

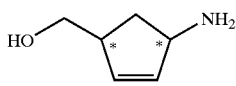
IV comprising:

a) converting a racemic 1-amino-4-(hydroxymethyl) cyclopent-2-ene derivative of the general formula

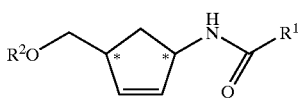
III wherein $R^1$, as defined in claim 1, using a hydrolase in the presence of an acylating agent into enantiomerically enriched

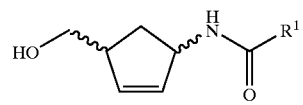
I

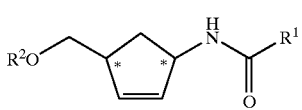
II wherein $R^1$ and $R^2$, as defined in claim 1; and b) chemically hydrolyzing the 1-amino-4-(hydroxymethyl)cyclopent-2-ene derivatives of the general formulae I and II into the corresponding enantiomerically enriched 1-amino-4-(hydroxymethyl)cyclopent-2-ene isomers of the formula IV.

The starting materials, the racemic 1-amino-4-(hydroxymethyl)cyclopent-2-ene derivatives of the general formula III, can be prepared starting from (±)-2-azabicyclo[2.2.1]hept-5-ene-3-one, in accordance with WO 97/45529. Preference is given to using the cis-racemic starting materials.

The term alkyl, as used in this context, includes both linear and branched alkyl. Alkyl can be substituted or unsubstituted. $C_{1-8}$-alkyl is in particular methyl, ethyl, propyl, isopropyl, butyl, tert-butyl, pentyl and its isomers, hexyl and its isomers, heptyl and its isomers or octyl and its isomers. Substituted $C_{1-8}$-alkyl is understood as $C_{1-8}$-alkyl which is substituted by one or more halogen atoms, by $OR^3$ or by $NR^3R^4$, $R^3$ and $R^4$ being identical or different and being hydrogen or branched or linear $C_{1-8}$-alkyl, aryl or cycloalkyl. The halogen atom used may be F, Cl, Br or I. Examples of $NR^3R^4$s are methylamino, N-methyl-N-ethylamino, 1-piperidinyl or aminomethyl. Examples of $OR^3$s are methoxy, methoxymethyl, ethoxy, propoxy and phenoxy.

Aryl is preferably understood as benzyl or phenyl, substituted or unsubstituted. Substituted aryl is understood hereinbelow as aryl which is substituted by one or more halogen atoms $C_{1-4}$-alkyl groups, $C_{1-4}$-alkoxy groups, amino, cyano or nitro groups. The substituted benzyl used is preferably chloro- or bromobenzyl, and the substituted phenyl used is preferably bromo- or chlorophenyl. Cycloalkyl is advantageously substituted or unsubstituted $C_{3-7}$-cycloalkyl, for example cyclopropyl, cyclopentyl or cyclohexyl. Examples of suitable substituents are those mentioned for aryl.

Acyl corresponds to the acid component of the acylating agent used.

Acyl is preferably $C_{1-6}$-alkanoyl, unsubstituted or substituted by one or more halogen atoms, $C_{1-4}$-alkoxy, aryl, hydroxy, amino, cyano, nitro, and/or COOR, where R is $C_{1-4}$-alkyl. Examples of unsubstituted or substituted acyl radicals are acetyl, propionyl, butyryl, chloroacetyl, bromoacetyl, dichloroacetyl, cyanoacetyl, methoxycarbonyl, ethoxycarbonyl, methoxyethanoyl, hydroxybutyroyl, hydroxyhexanoyl, phenylcarbonyl, chlorophenylcarbonyl and benzylcarbonyl.

Suitable acylating agents are, in general, carboxylic acid derivatives, such as carboxamides, carboxylic anhydrides or carboxylic esters.

The carboxylic esters used may be alkoxycarboxylic esters, such as ethyl methoxyacetate, or propyl methoxyacetate, $C_{1-6}$-carboxylic esters, such as butyl acetate, ethyl butyrate, phenyl butyrate, trichloroethyl butyrate, ethyl hexanoate, vinyl butyrate, glycerol esters, such as tributyrin (glyceryl tributyrate), glycol esters, such as glycol dibutyrate, diethyl diglycolate, or dicarboxylic esters, such as vinyl succinate, cyano-substituted esters, such as cyanoacetic esters, or cyclic carboxylic esters, such as butyrolactone, caprolactone.

The carboxamides used may be the amides which correspond to the abovementioned esters.

The carboxylic anhydrides used may be simple, mixed or cyclic anhydrides, such as butyric anhydride, acetyl benzoate, succinic anhydride.

The hydrolases used may be lipases, esterases or proteases. Suitable for use as lipase are customary lipases, such as, for example, Novo-Lipase SP523 from *Aspergillus oryzae* (Novozym 398), Novo-Lipase SP524 from *Aspergil-* lus oryzae (Lipase=Palatase 20000L from Novo), Novo-Lipase SP525 from *Candida antarctica* (Lipase B Novozym 435, immobilized), Novo-Lipase SP526 from *Candida antarctica* (Lipase A=Novozym 735, immobilized), Lipase kits from Fluka (1 & 2), Amano P Lipase, lipase from Pseudomonas sp., lipase from *Candida cylindracea*, lipase from *Candida lipolytica*, lipase from *Mucor miehei*, lipase M from *Mucor javanicus* (Amano), lipase from *Aspergillus niger*, lipase from *Bacillus thermocatenulatus*, lipase from *Candida antarctica*, Lipase AH (Amano; immobilized), Lipase P (Nagase), Lipase AY from *Candida rugosa*, Lipase G (Amano 50), Lipase F (Amano F-AP15), Lipase PS (Amano), Lipase AH (Amano), Lipase D (Amano), Lipase AK from *Pseudomonas fluorescens*, Lipase PS from *Pseudomonas cepacia*, Newlase I from *Rhizopus niveus*, Lipase PS-CI (immobilized lipase from *Pseudomonas cepacia*).

These lipases can be used, as is known to the person skilled in the art, as cell-free enzyme extracts or else in the corresponding microorganism cell.

Suitable proteases are likewise commercially available proteases, for example serine proteases such as subtilisin. The subtilisin used may be, for example, savinase from Bacillus sp., alcalase, subtilisin from *Bacillus licheniformis* and proteases from Aspergillus, Rhizopus, Streptomyces or Bacillus sp.

Depending on which hydrolase is selected, one of the two enantiomers of a racemic, for example cis-racemic, 1-amino-4-(hydroxymethyl)cyclopent-2-ene of the formula III is acylated (compounds of the formula I), whereas the other enantiomer remains unchanged (compounds of the formula II). The two enantiomers can then be separated.

Different hydrolases may have different stereospecificities. If, for example, cis-N-acetyl-1-amino-4-(hydroxymethyl)cyclopent-2-ene is reacted with lipase M and an acylating agent, the (1R, 4S)-enantiomer is acylated specifically and can be separated from the non-acylated (1S, 4R)-enantiomer. If the hydrolase used is, for example, Savinase (protease from Bacillus sp.), the (1S, 4R)-enantiomer is acylated specifically, whereas the (1R, 4S)-enantiomer remains.

The hydrolase-catalyzed acylation is advantageously carried out at a temperature of from 0 to 70° C., preferably at a temperature of from 15 to 45° C.

The hydrolase-catalyzed acylation can be carried out in a protic or aprotic organic solvent. Suitable aprotic organic solvents are ethers, aliphatic hydrocarbons, organic bases and carboxylic acid derivatives. Ethers which may be used are tert-butyl methyl ether, diisopropyl ether, dibutyl ether, dioxane or tetrahydrofuran. Suitable aliphatic hydrocarbons are hexane, heptane, octane. Suitable organic bases are pyridines or trialkylamines, such as triethylamine. Possible carboxylic acid derivatives are, for example, ethyl acetate or the above-described acylating agents.

The enantiomerically enriched 1-amino-4-(hydroxymethyl)cyclopent-2-ene derivatives of the general formula I or II formed in the hydrolase-catalyzed acylation can, after separation, be directly chemically hydrolyzed into the corresponding enantiomerically enriched 1-amino-4-(hydroxymethyl)-cyclopent-2-ene isomers of the formula IV

IV

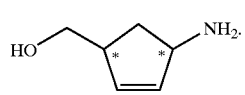

Alternatively, the enantiomerically enriched 1-amino-4-(hydroxymethyl)cyclopent-2-ene derivative of the general formula I which has been separated off can initially, by choosing the appropriate hydrolysis conditions, be hydrolysed step-wise back to the corresponding enantiomerically enriched 1-amino-4-(hydroxymethyl)cyclopent-2-ene derivative of the general formula II which, if desired, is then converted by further chemical hydrolysis as above into the corresponding enantiomerically enriched 1-amino-4-(hydroxymethyl)cyclopent-2-ene of the formula IV.

Advantageously, the chemical hydrolysis is carried out using an alkali metal hydroxide or ammonia. The alkali metal hydroxide used may be sodium hydroxide or potassium hydroxide.

The chemical hydrolysis can be carried out at a temperature of from 20 to 100° C., preferably at a temperature of from 60 to 80° C.

The preferred enantiomerically enriched 1-amino-4-(hydroxymethyl)cyclopent-2-ene derivative of the general formula I is the (1R,4S)- and (1S,4R)-N-acetyl-1-amino-4-(propylcarbonyloxymethyl)cyclopent-2-ene ($R^1=CH_3$, $R^2$=propylcarbonyl), and the preferred 1-amino-4-(hydroxymethyl)cyclopent-2-ene derivatives of the general formula II are the (IR,4S)- and (1S,4R)-N-acetyl-1-amino-4-(hydroxymethyl)cyclopent-2-ene, which are then chemically hydrolyzed preferably into the (IR,4S)- or (1S,4R)-1-amino-4-(hydroxymethyl)cyclopent-2-ene.

EXAMPLES

Example 1

50 mg of cis-N-acetyl-1-amino-4-(hydroxymethyl)cyclopent-2-ene and 250 µl of vinyl butyrate were dissolved in 5 ml of 2-methyl-2-butanol. 300 mg of Lipase M (from Mucor javanicus; Amano) were added, and the suspension was stirred at room temperature. After 16 h, (1S,4R)-N-acetyl-1-amino-4-(hydroxymethyl)cyclo-pent-2-ene was present in an enantiomeric excess of 98.5% (GC).

After separating (1S,4R)-N-acetyl-1-amino-4-(hydroxymethyl)cyclopent-2-ene and the (1R,4S)-N-acetyl-1-amino-4-(propylcarbonyloxymethyl)cyclopent-2-ene formed (chromatography over silica gel 60), the two compounds were separately taken up in 2M aqueous sodium hydroxide solution. (1S, 4R)-N-acetyl-1-amino-4-(hydroxymethyl)cyclopent-2-ene was converted by stirring at 80° C. (70 h), into the enantiomerically pure or enantiomerically enriched cis-1-amino-4-(hydroxymethyl)cyclopent-2-ene while (1R, 4S)-N-acetyl-1-amino-4-(propylcarbonyloxymethyl)cyclopent-2-ene was converted by stirring at room temperature (5 h) into the enantiomerically pure or enantiomerically enriched cis-N-acetyl-1-amino-4-(hydroxymethyl)cyclopent-2-ene.

Example 2

10 mg of cis-N-acetyl-1-amino-4-(hydroxymethyl)cyclopent-2-ene and 50 µl of vinyl butyrate were dissolved in 1 ml of dioxane. 30 mg of Lipase M (from Mucor javanicus; Amano) were added, and the suspension was stirred at room temperature. After 20 h, (1S,4R)-N-acetyl-1-amino-4-(hydroxymethyl)cyclopent-2-ene was present in an enantiomeric excess of 91.0% (GC).

Example 3

10 mg of cis-N-acetyl-1-amino-4-(hydroxymethyl)cyclopent-2-ene and 50 µl of vinyl butyrate were dissolved in 1 ml of 2-methyl-2-butanol. 40 mg of savinase (protease from Bacillus sp.; Novo Nordisk) were added, and the suspension was stirred at room temperature. After 20 h, (1R,4S)-N-acetyl-1-amino-4-(hydroxymethyl)cyclopent-2-ene was present in an enantiomeric excess of 91.7% (GC).

Example 4

10 mg of cis-N-acetyl-1-amino-4-(hydroxymethyl) cyclopent-2-ene and 50 µl of vinyl butyrate were dissolved in 1 ml of dioxane. 40 mg of savinase (protease from Bacillus sp.; Novo Nordisk) were added, and the suspension was stirred at room temperature. After 200 h, (1R,4S)-N-acetyl-1-amino-4-(hydroxy-methyl)cyclopent-2-ene was present in an enantiomeric excess of 81.7% (GC).

Example 5

100 mg of cis-N-acetyl-1-amino-4-(hydroxymethyl) cyclopent-2-ene and 0.5 mmol of vinyl butyrate were dissolved in 1 ml of 2-methyl-2-butanol. 20 mg of Lipase PS (from *Pseudomonas cepacia*) were added, and the suspension was stirred at room temperature. After 21 h, (1R,4S)-N-acetyl-1-amino-4-(hydroxymethyl)-cyclopent-2-ene is present in an enantiomeric excess of 44% (GC).

Example 6

10 mg of cis-N-acetyl-1-amino-4-(hydroxymethyl) cyclopent-2-ene and 0.03 mmol of tributyrin were dissolved in 1 ml of 2-methyl-2-butanol. 20 mg of Lipase PS (*Pseudomonas cepacia*) were added, and the suspension was stirred at room temperature. After 200 h, (1R,4S)-N-acetyl-1-amino-4-(hydroxymethyl)-cyclopent-2-ene is present in an enantiomeric excess of 32% (GC).

What is claimed is:

1. A process for preparing enantiomerically enriched 1-amino-4-(hydroxymethyl) cyclopent-2-ene derivatives of the general formulae:

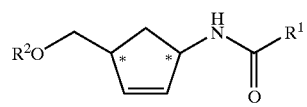

I

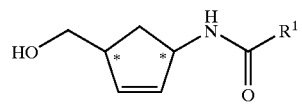

II wherein $R^1$ is hydrogen or an optionally substituted $C_{1-8}$-alkyl radical, aryl radical or cycloalkyl radical and $R^2$ is acyl, comprising reacting a racemic 1-amino-4-(hydroxymethyl) cyclopent-2-ene derivative of the general formula:

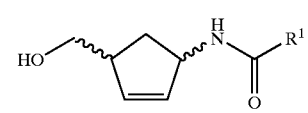

III in which $R^1$, as defined above, with a hydrolase in the presence of an acylating agent.

2. The process of claim 1, wherein the hydrolase used is a protease, esterase or lipase.

3. The process of claim 1 wherein the hydrolase-catalyzed acylation is carried out at a temperature of from 0 to 70° C.

4. The process of claim 1 wherein the hydrolase-catalyzed acylation is carried out in a protic or aprotic organic solvent.

5. A process for preparing enantiomerically enriched 1-amino-4-(hydroxymethyl) cyclopent-2-ene derivatives of the general formula:

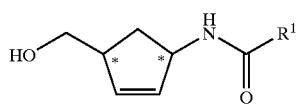

II comprising a) converting a racemic 1-amino-4-(hydroxymethyl) cyclopent-2-ene derivative of the general formula:

III in which $R^1$, as defined in claim 1; using a hydrolase in the presence of an acylating agent into enantiomerically enriched

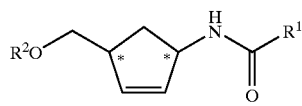

I wherein $R^1$ and $R^2$, as defined in claim 1; and b) chemically hydrolyzing the 1-amino-4-(hydroxymethyl) cyclopent-2-ene derivatives of the general formula I into the corresponding enantiomers of the general formula II.

6. The process of claim 5, wherein the chemical hydrolysis is carried out at a temperature of from 20 to 100° C.

7. A process for preparing enantiomerically enriched 1-amino-4-(hydroxymethyl) cyclopent-2-ene of the formula:

IV comprising:

a) converting a racemic 1-amino-4-(hydroxymethyl) cyclopent-2-ene derivative of the general formula:

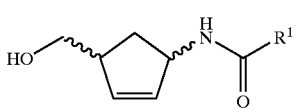

III wherein $R^1$, as defined in claim 1, using a hydrolase in the presence of an acylating agent into enantiomerically enriched

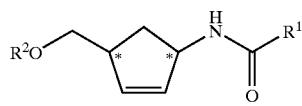

I

-continued
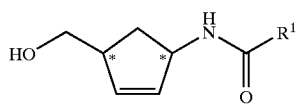
II
b) chemically hydrolyzing the 1-amino-4-(hydroxymethyl) cyclopent-2-ene derivatives of the general formulae I and II into the corresponding enantiomerically enriched 1-amino-4-(hydroxymethyl) cyclopent-2-ene isomers of the formula IV.
* * * * *